United States Patent
Maltz et al.

(10) Patent No.: US 11,534,627 B2
(45) Date of Patent: Dec. 27, 2022

(54) SYSTEMS AND METHODS FOR TREATMENT POSITIONING

(71) Applicant: SHANGHAI UNITED IMAGING HEALTHCARE CO., LTD., Shanghai (CN)

(72) Inventors: Jonathan Maltz, Walnut Creek, CA (US); Supratik Bose, Walnut Creek, CA (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 335 days.

(21) Appl. No.: 16/796,805

(22) Filed: Feb. 20, 2020

(65) Prior Publication Data
US 2021/0260407 A1    Aug. 26, 2021

(51) Int. Cl.
*A61N 5/10* (2006.01)
*G01N 23/20* (2018.01)
(Continued)

(52) U.S. Cl.
CPC ............ *A61N 5/1049* (2013.01); *A61B 6/032* (2013.01); *A61B 6/0407* (2013.01); *A61B 6/4078* (2013.01); *A61N 2005/1091* (2013.01)

(58) Field of Classification Search
CPC ....... A61B 6/4078; A61B 6/032; A61B 6/486; A61B 6/04; A61B 6/5217; A61B 6/0407;
(Continued)

(56) References Cited

U.S. PATENT DOCUMENTS 9,248,312 B2 *   2/2016   Li ..................... A61N 5/1049
9,687,200 B2 *   6/2017   Maurer, Jr. ............ A61B 6/032
(Continued)

FOREIGN PATENT DOCUMENTS

CN         2191631 Y      3/1995
CN       103054607 A      4/2013
(Continued)

OTHER PUBLICATIONS

First Office Action in Chinese Application No. 202011453332.7 dated Apr. 25, 2022, 13 pages.

*Primary Examiner* — Irakli Kiknadze
(74) *Attorney, Agent, or Firm* — Metis IP LLC

(57) ABSTRACT

System for treatment positioning is provided. The system may include a treatment component, an imaging component, and a couch. The treatment component may include a radiation source that has a radiation isocenter. The couch may be movable between the treatment component and the imaging component, and include a positioning line that has a positioning feature. The system may acquire at least one first image relating to a subject and the positioning line using the radiation source at a set-up position. The system may also acquire at least one second image relating to the subject and the positioning line using the imaging component at an imaging position. The system may further determine a treatment isocenter of a target of the subject based on the at least one second image, and determine a treatment position of the subject based on the first image(s), the second image(s), and the positioning line.

20 Claims, 8 Drawing Sheets

(51) Int. Cl.
*A61B 6/03* (2006.01)
*A61B 6/04* (2006.01)
*A61B 6/00* (2006.01)

(58) Field of Classification Search
CPC ......... A61B 8/40; A61B 6/5235; A61B 6/037;
A61B 6/4035; A61B 6/548; A61B 6/107;
A61B 6/06; A61B 6/461; A61B 6/5205;
A61B 6/5264; A61B 6/4458; A61B 6/54;
A61B 6/469; A61B 6/4405; A61B
6/4441; A61B 6/487; A61B 6/504; A61B
6/4447; A61B 6/027; A61B 6/503; A61B
6/0487; A61B 6/541; A61B 6/5258; A61B
6/547; A61B 8/085; A61B 8/4227; A61B
8/4209; A61B 6/5288; A61B 6/5223;
A61B 6/12; A61B 6/48; A61B 6/5229;
A61B 6/4085; A61B 6/4435; A61B 6/44;
A61B 6/4208; A61N 5/1049; A61N
2005/1091; A61N 2005/1061; A61N 5/10;
A61N 5/1068; A61N 5/1067; A61N
2005/1059; A61N 2005/1051; A61N
2005/1052; A61N 5/103; A61N 5/1065;
A61N 5/1077; A61N 5/107; A61N
5/1071; A61N 5/1039; A61N 5/1037;
A61N 2005/1062; A61N 5/1082; A61N
5/1045; A61N 5/1036; A61N 5/1083;
A61N 5/1075; A61N 5/1081; A61N
5/1069; A61N 2005/1055; A61N 5/1048;
A61N 5/1064; A61N 2005/1076; A61N
2005/1057; A61N 2005/1054; A61N
2005/1074; G21K 1/046; G06T 7/215;
G06T 7/0016; G06T 11/005; G06T
2207/30096; G06T 2207/10128; G06T
7/0012; G06T 7/246; G06T 11/003; G06T
11/008; G06T 7/20; G06T 2207/10076;
G06T 2207/10124; G06T 2207/10081;
G06T 2211/412; G06T 2207/30241;
G06T 9/20; G06T 7/33; G03H 1/2249;
G03H 1/02; G03H 5/00; G01B 11/00;
G16H 50/50; G16H 50/30
USPC ...... 378/4, 19, 20, 64, 65, 69, 208, 209, 70;
600/427

See application file for complete search history.

(56) References Cited

U.S. PATENT DOCUMENTS

| | | | |
|---|---|---|---|
| 9,901,750 B2 * | 2/2018 | Shapiro | A61B 6/4085 |
| 11,147,989 B2 * | 10/2021 | Cox | A61N 5/1039 |
| 11,179,129 B2 * | 11/2021 | Harrington | A61B 6/5217 |
| 2013/0163724 A1 | 6/2013 | Marash et al. | |
| 2016/0202864 A1 | 7/2016 | Hardie et al. | |
| 2020/0129785 A1 | 4/2020 | Li et al. | |
| 2020/0353287 A1 | 11/2020 | Maltz | |

FOREIGN PATENT DOCUMENTS

| | | | |
|---|---|---|---|
| CN | 104587609 A | 5/2015 | |
| CN | 108744305 A | 11/2018 | |
| CN | 110582328 A | 12/2019 | |
| WO | WO-2020006500 A1 * | 1/2020 | A61B 6/027 |

* cited by examiner

SYSTEMS AND METHODS FOR TREATMENT POSITIONING

TECHNICAL FIELD

The present disclosure generally relates to systems and methods for radiotherapy (RT), and more particularly, to systems and methods for treatment positioning.

BACKGROUND

Radiotherapy is widely used in clinical treatment for cancers and other conditions of a patient. Conventionally, before a radiotherapy treatment on a patient (e.g., a cancer patient), a planning image (e.g., a computed tomography (CT) image, a magnetic resonance imaging (MRI) image) of the cancer patient may be acquired. A treatment plan for the cancer patient may be made based on the planning image. Following the treatment plan, a treatment may be delivered to the patient during several treatment sessions, spreading over a treatment period of multiple days (e.g., 2 to 5 weeks). However, during the treatment period, an anatomical change (e.g., weight loss or gain, growth, shrinkage, or disappearance of a tumor, the appearance of a new tumor, etc.) may take place within the body of the patient. The size and/or position of a certain organ may change between the planning and the time of a specific treatment session. Accordingly, before or during a current treatment session, a treatment image of the patient may be acquired and an anatomical change within the patient may be determined by registering the planning image and the treatment image.

In a non-in-situ image guided radiation therapy (IGRT) system, the treatment image in a current treatment session may be acquired using a non-in-situ imaging device which is spaced by a distance from a treatment device. The patient may need to be moved to different positions for imaging and treatment. In such cases, a treatment position that aligns a treatment isocenter of the patient with a radiation isocenter of the treatment device may need to be determined, in order to improve the accuracy of delivery of the current treatment session. Conventionally, couch encoder positions may be used to measure the distance that the couch travels between the treatment device and the non-in-situ imaging device, which may be vulnerable to inaccuracies caused by, e.g., a mechanical error of the couch (e.g., an angular deviation of the couch trajectory from an ideal moving direction). In addition, a calibration may need to be performed to facilitate the position adjustment of the patient based on the treatment image when the patient is situated within the treatment device, which is time-consuming and increases the effort on the part of an operator (e.g., a doctor) of the treatment device. Thus, it is desirable to develop systems and methods for treatment positioning in non-in-situ IGRT systems, thereby obviating the need for calibration and improving the accuracy of treatment positioning and delivery.

SUMMARY

According to an aspect of the present disclosure, a system for treatment positioning is provided. The system may include a treatment component, an imaging component, and a couch. The treatment component may be used to treat a target of a subject and include a radiation source that has a radiation isocenter. The couch may be movable between the treatment component and the imaging component along a reference axis. The couch may include a positioning line that has a positioning feature. The positioning feature may have a plurality of feature values. Each feature value may correspond to a unique cross section of the couch. The unique cross section may be at an oblique angle with the reference axis. The system may also include at least one storage device storing a set of instructions, and at least one processor configured to communicate with the at least one storage device. When executing the set of instructions, the at least one processor may be configured to direct the system to perform the following operations. The system may acquire at least one first image relating to the subject and the positioning line using the radiation source of the treatment component. The subject may be located at a set-up position with respect to the treatment component during the acquisition of the at least one first image. The system may also acquire at least one second image relating to the subject and the positioning line using the imaging component. The subject may be located at an imaging position with respect to the imaging component during the acquisition of the at least one second image. The system may also determine a treatment isocenter of the target based on the at least one second image. The system may further determine a treatment position of the subject based on the at least one first image, the at least one second image, and the positioning line. The treatment isocenter of the target may align with the radiation isocenter when the subject is located at the treatment position.

In some embodiments, to determine a treatment position of the subject, the system may further determine, based on the at least one first image, a first position of the radiation isocenter with respect to the positioning line during the acquisition of the at least one first image. The system may also determine, based on the at least one second image, a second position of the treatment isocenter with respect to the positioning line during the acquisition of the at least one second image. The system may also determine the treatment position of the subject based on the first position, the second position, and the positioning line.

In some embodiments, to determine the treatment position of the subject based on the first position, the second position, and the positioning line, the system may further determine an offset between the set-up position and the treatment position based on the first position, the second position, and the positioning line. The system may also determine the treatment position based on the offset and the set-up position.

In some embodiments, the at least one first image may include a plurality of 2-dimensional (2D) images relating to a first intersection between the positioning line and an isocentric plane of the radiation source when the subject is located at the set-up position. The isocentric plane may pass through the radiation isocenter and perpendicular to the reference axis. To determine a first position of the radiation isocenter with respect to the positioning line during the acquisition of the at least one first image, the system may further determine, based on the plurality of 2D images, a position of the radiation isocenter with respect to the first intersection. The system may also determine, based on at least one of the plurality of 2D images, an angular orientation of the positioning line with respect to the reference axis.

In some embodiments, the at least one second image may include a three-dimensional (3D) image of the subject. To determine a second position of the treatment isocenter with respect to the positioning line during the acquisition of the at least one second image, the system may further identify an image plane from the 3D image of the subject. The image plane may pass through the treatment isocenter and be perpendicular to the reference axis. The system may also determine a second intersection between the image plane and the positioning line when the subject is located at the imaging position. The system may also determine a position of the treatment isocenter with respect to the second intersection.

In some embodiments, the system may further place the subject at the set-up position before the acquisition of the at least one first image. The system may also cause the couch to move the subject from the set-up position to the imaging position after the acquisition of the at least one first image and before the acquisition of the at least one second image.

In some embodiments, the treatment component may include a megavoltage (MV) treatment source as the radiation source, or the treatment component may include an MV treatment source and a kilovoltage (KV) radiation source, and the radiation source may be the KV radiation source.

In some embodiments, the imaging component may be a fan-beam computed tomography (FBCT) device.

In some embodiments, the positioning line may have one of an N-shape, an S-shape, a V-shape, a W-shape, a triangle, a trapezoid, a polygon, or an irregular shape.

According to another aspect of the present disclosure, a method for treatment positioning implemented on a system is provided. The system may include a treatment component, an imaging component, and a couch. The treatment component may be used for treating a target of a subject and include a radiation source that has a radiation isocenter. The couch may be movable between the treatment component and the imaging component along a reference axis. The couch may include a positioning line that has a positioning feature. The positioning feature may have a plurality of feature values. Each feature value may correspond to a unique cross section of the couch. The unique cross section may be at an oblique angle with the reference axis. The method may include acquiring, using the radiation source of the treatment component, at least one first image relating to the subject and the positioning line. The subject may be located at a set-up position with respect to the treatment component during the acquisition of the at least one first image. The method may also include acquiring, using the imaging component, at least one second image relating to the subject and the positioning line. The subject may be located at an imaging position with respect to the imaging component during the acquisition of the at least one second image. The method may also include determining, based on the at least one second image, a treatment isocenter of the target. The method may further include determining a treatment position of the subject based on the at least one first image, the at least one second image, and the positioning line. The treatment isocenter of the target may align with the radiation isocenter when the subject is located at the treatment position.

In some embodiments, to determine a treatment position of the subject, the method may further include determining, based on the at least one first image, a first position of the radiation isocenter with respect to the positioning line during the acquisition of the at least one first image. The method may also include determining, based on the at least one second image, a second position of the treatment isocenter with respect to the positioning line during the acquisition of the at least one second image. The method may also include determining, based on the first position, the second position, and the positioning line, the treatment position of the subject.

In some embodiments, to determine the treatment position of the subject based on the first position, the second position, and the positioning line, the method may further include determining, based on the first position, the second position, and the positioning line, an offset between the set-up position and the treatment position. The method may also include determining, based on the offset and the set-up position, the treatment position.

In some embodiments, the at least one first image may include a plurality of two-dimensional (2D) images relating to a first intersection between the positioning line and an isocentric plane of the radiation source when the subject is located at the set-up position. The isocentric plane may pass through the radiation isocenter and being perpendicular to the reference axis. To determine a first position of the radiation isocenter with respect to the positioning line during the acquisition of the at least one first image, the method may further include determining, based on the plurality of 2D images, a position of the radiation isocenter with respect to the first intersection. The method may also include determining, based on at least one of the plurality of 2D images, an angular orientation of the positioning line with respect to the reference axis.

In some embodiments, the at least one second image may include a three-dimensional (3D) image of the subject. To determine a second position of the treatment isocenter with respect to the positioning line during the acquisition of the at least one second image, the method may further include identifying, from the 3D image of the subject, an image plane that passes through the treatment isocenter and is perpendicular to the reference axis. The method may also include determining a second intersection between the image plane and the positioning line when the subject is located at the imaging position. The method may also include determining a position of the treatment isocenter with respect to the second intersection.

In some embodiments, the method may further include placing the subject at the set-up position before the acquisition of the at least one first image. The method may also include causing the couch to move the subject from the set-up position to the imaging position after the acquisition of the at least one first image and before the acquisition of the at least one second image.

In some embodiments, the treatment component may include a megavoltage (MV) treatment source as the radiation source, or the treatment component may include an MV treatment source and a kilovoltage (KV) radiation source, and the radiation source may be the KV radiation source.

In some embodiments, the imaging component may be a fan-beam computed tomography (FBCT) device.

In some embodiments, the positioning line may have one of an N-shape, an S-shape, a V-shape, a W-shape, a triangle, a trapezoid, a polygon, or an irregular shape.

According to another aspect of the present disclosure, a non-transitory computer readable medium is provided. The non-transitory computer readable medium may include at least one set of instructions for treatment positioning in a system. The system may include a treatment component, an imaging component, and a couch. The treatment component may be used for treating a target of a subject and include a radiation source that has a radiation isocenter. The couch may be movable between the treatment component and the imaging component along a reference axis. The couch may include a positioning line that has a positioning feature. The positioning feature may have a plurality of feature values. Each feature value may correspond to a unique cross section of the couch. The unique cross section may be at an oblique angle with the reference axis. When executed by one or more processors of the system, the at least one set of instructions may cause the system to perform a method. The method may include acquiring, using the radiation source of the treatment component, at least one first image relating to the subject and the positioning line. The subject may be located at a set-up position with respect to the treatment component during the acquisition of the at least one first image. The method may also include acquiring, using the imaging component, at least one second image relating to the subject and the positioning line. The subject may be located at an imaging position with respect to the imaging component during the acquisition of the at least one second image. The method may also include determining a treatment isocenter of the target based on the at least one second image. The method may further include determining a treatment position of the subject based on the at least one first image, the at least one second image, and the positioning line. The treatment isocenter of the target may align with the radiation isocenter when the subject is located at the treatment position.

In some embodiments, to determine a treatment position of the subject, the method may further include determining, based on the at least one first image, a first position of the radiation isocenter with respect to the positioning line during the acquisition of the at least one first image. The method may also include determining, based on the at least one second image, a second position of the treatment isocenter with respect to the positioning line during the acquisition of the at least one second image. The method may also include determining, based on the first position, the second position, and the positioning line, the treatment position of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
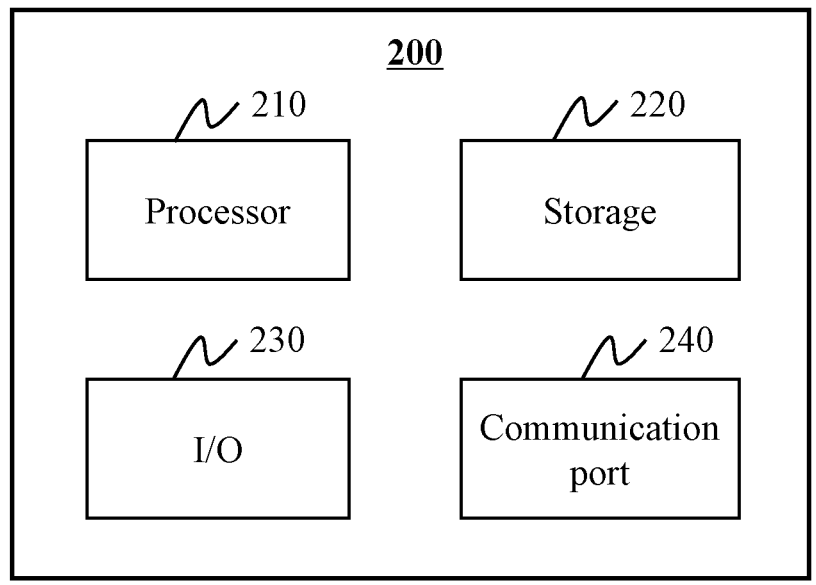
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging and/or treatment, such as for disease diagnosis, treatment or research purposes. In some embodiments, the systems may include an RT system, a computed tomography (CT) system, an emission computed tomography (ECT) system, an X-ray photography system, a positron emission tomography (PET) system, or the like, or any combination thereof. For illustration purposes, the disclosure describes systems and methods for radiotherapy.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a planning image, or a treatment image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

An aspect of the present disclosure relates to systems and methods for treatment positioning. The systems may include a treatment component, an imaging component, and a couch. The treatment component may be used to treat a target of a subject and include a radiation source that has a radiation isocenter. The couch may be movable between the treatment component and the imaging component along a reference axis. The couch may include a positioning line that has a positioning feature. The positioning feature may have a plurality of feature values, each of which may correspond to a unique cross section of the couch. The systems and methods may acquire at least one first image relating to the subject and the positioning line using the radiation source of the treatment component. The subject may be located at a set-up position with respect to the treatment component during the acquisition of the at least one first image. The systems and methods may also acquire at least one treatment image (or referred to as at least one second image) relating to the subject and the positioning line using the imaging component. The subject may be located at an imaging position with respect to the imaging component during the acquisition of the at least one treatment image. The systems and methods may further determine a treatment isocenter of the target based on the at least one treatment image, and determine a treatment position of the subject based on the at least one first image, the at least one treatment image, and the positioning line. The treatment isocenter of the target may align with the radiation isocenter when the subject is located at the treatment position.

According to some embodiments of the present disclosure, the subject may be positioned at the set-up position before a current treatment session. The radiation source of the treatment component (e.g., a treatment radiation source or an additional radiation source) may be used to perform a scan (e.g., a tomographic imaging) of the subject at the set-up position, wherein resulting image(s) of the scan (e.g., the at least one first image) may be used to determine a first position of the radiation isocenter with respect to the positioning line during the scan. Based on the treatment image acquired at the imaging position, a second position of the treatment isocenter of the subject with respect to the positioning line during the acquisition of the treatment image may be determined. By taking the positioning line as a reference substance and based on the first position and the second position, the treatment position may be determined. In this way, there is no need to perform a calibration based on the positioning line, which may improve the accuracy and efficiency of treatment positioning and delivery. Additionally, in some embodiments, the treatment radiation source of the treatment component may be used as the radiation source that performs the scan on the subject at the set-up position, which may simplify the system for treatment positioning.

Figure 1:
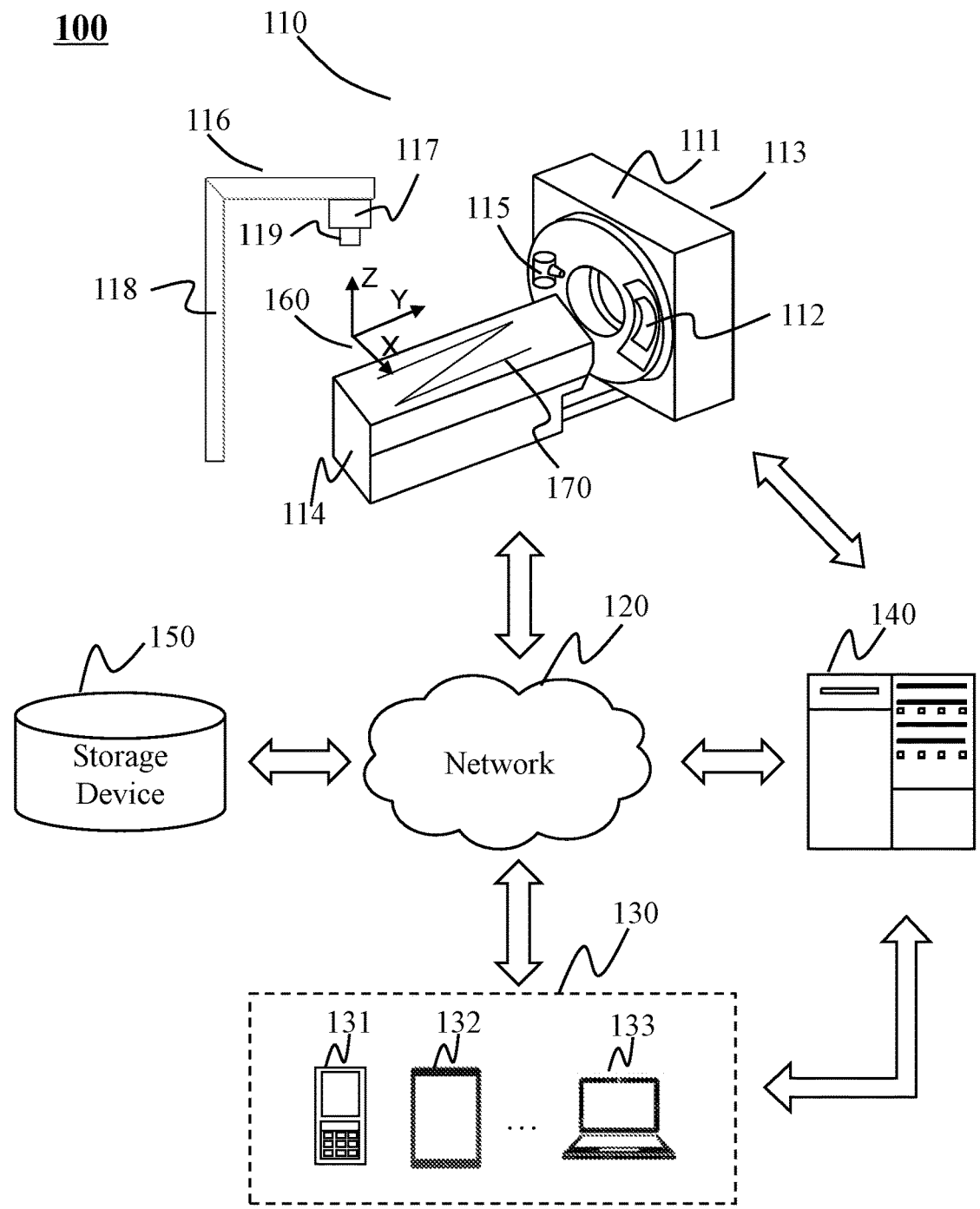
FIG. 1 is a schematic diagram illustrating an exemplary RT system according to some embodiments of the present disclosure.

FIG. 1 is a schematic diagram illustrating an exemplary RT system 100 according to some embodiments of the present disclosure. The RT system 100 may include a radiation delivery device 110, a network 120, one or more terminals 130, a processing device 140, and a storage device 150. In some embodiments, two or more components of the RT system 100 may be connected to and/or communicate with each other via a wireless connection (e.g., the network 120), a wired connection, or a combination thereof. The connection between the components of the RT system 100 may be variable. Merely by way of example, the radiation delivery device 110 may be connected to the processing device 140 through the network 120 or directly. As a further example, the storage device 150 may be connected to the processing device 140 through the network 120 or directly. As still another example, the terminal(s) 130 may be connected to the processing device 140 directly or through the network 120.

In some embodiments, the radiation delivery device 110 may be an RT device. The RT device may be configured to deliver a radiotherapy treatment for cancers and other conditions. For example, the RT device may deliver one or more radiation beams to a treatment region (e.g., a tumor) of a subject (e.g., a patient) for causing an alleviation of the subject's symptom. In some embodiments, the RT device may be a conformal radiation therapy device, an image guided radiation therapy (IGRT) device, an intensity modulated radiation therapy (IMRT) device, an intensity modulated arc therapy (IMAT) device, or the like.

As illustrated in FIG. 1, the radiation delivery device 110 may include an imaging component 113, a treatment component 116, a couch 114, or the like. The imaging component 113 may be configured to acquire an image of a subject prior to a radiotherapy treatment, during the radiotherapy treatment, and/or after the radiotherapy treatment. The subject may include any biological subject (e.g., a human being, an animal, a plant, or a portion thereof) and/or a non-biological subject (e.g., a phantom). For example, the imaging component 113 may include a computed tomography (CT) device (e.g., a cone beam computed tomography (CBCT) device, a fan-beam computed tomography (FBCT) device), an ultrasound imaging device, a fluoroscopy imaging device, a magnetic resonance imaging (MRI) device, a single photon emission computed tomography (SPECT) device, a positron emission tomography (PET) device, an X-ray imaging device, or the like, or any combination thereof. For illustration purposes, the present disclosure takes a CT device as an exemplary imaging component 113. This is not intended to be limiting.

In some embodiments, the imaging component 113 may include an imaging radiation source 115, a detector 112, a gantry 111, or the like. The imaging radiation source 115 and the detector 112 may be mounted on the gantry 111. The imaging radiation source 115 may emit radioactive rays to the subject. The detector 112 may detect radiation events (e.g., x-ray photons, gamma-ray photons) emitted from the imaging region of the imaging component 113. In some embodiments, the detector 112 may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The treatment component 116 may be configured to deliver a radiotherapy treatment to the subject. The treatment component 116 may include a treatment head and a gantry 118. In some embodiments, the treatment head may include a treatment radiation source 117, a collimator 119, etc. The treatment radiation source 117 may be configured to generate and emit a radiation beam toward the subject for treatment. The collimator 119 may be configured to control the shape of the radiation beam generated by the treatment radiation source 117. In some embodiments, the radiation beam emitted by the treatment radiation source 117 may include electrons, photons, or other types of radiation. In some embodiments, the energy of the radiation beam may be in the megavoltage range (e.g., >1 MeV), and may be referred to as a megavoltage (MV) beam. In some embodiments, the treatment radiation source 117 may include a linear accelerator (LINAC) configured to accelerate electrons, ions, or protons.

In some embodiments, the treatment component 116 may be used to treat as well as image (or referred to as scan) the subject. For example, the treatment radiation source 117 may be an MV treatment source for emitting an MV beam toward the subject. The treatment component 116 may include a detector opposite to the treatment radiation source 117 configured to detect radiations emitted from its detection region. The MV treatment source in combination with the detector of the treatment component 116 may be used to perform an MV imaging on the subject. Additionally or alternatively, the treatment component 116 may include a radiation source in addition to the treatment radiation source 117. The additional radiation source may emit radioactive rays (e.g., a particle ray, a photon ray) to the subject. For example, the additional radiation source may be configured to emit X-rays, which may be used to perform a CBCT scan, an FBCT scan, or the like, on the subject. In some embodiments, the additional radiation source may be an MV radiation source for emitting an MV beam or a kilovoltage (KV) radiation source for emitting a KV beam (i.e., a radiation beam whose energy is within the kilovoltage range (e.g., >1 KeV)). In some embodiments, the additional radiation source may be mounted on a same gantry (e.g., the gantry 118) as or a different gantry from the treatment radiation source 117. An isocenter of the additional radiation source may align with an isocenter of the treatment radiation source 117.

In some embodiments, the imaging component 113 may be spaced by a distance from the treatment component 116. In some embodiments, the gantry 111 of the imaging component 113 and the gantry 118 of the treatment component 116 may share an axis of rotation. The subject may be positioned in different positions on the couch 114 for imaging and treatment. In some embodiments, the imaging radiation source 115 and the treatment radiation source 117 may be integrated as one radiation source to image and/or treat the subject. In some embodiments, the imaging component 113 and the treatment component 116 may share a same gantry. For example, the treatment radiation source 117 may be mounted on the gantry 111 of the imaging component 113. A subject may be placed on the couch 114 for treatment and/or imaging.

The couch 114 may be configured to support the subject to be treated and/or imaged. In some embodiments, the couch 114 may be movable between the treatment component 116 and the imaging component 113 along a Y-axis direction of a coordinate system 160 as shown in FIG. 1. As used herein, the Y-axis direction may also be referred to as a reference direction (or axis) along which the couch 114 travels. The term "Y-axis direction" and the term "reference direction" (or "reference axis") may be used interchangeably in the present disclosure. In some embodiments, the couch 114 may be configured to rotate and/or translate along different directions so as to move the subject to a desired position (e.g., an imaging position under the imaging component 113 for imaging, a treatment position under the treatment component 116 for treatment, etc.).

In some embodiments, the couch 114 may include a positioning line 170 extending along the Y-axis direction. The positioning line 170 may be mounted on a surface of the couch 114 via any mounting mechanism, such as glue, adhesive, or the like. Alternatively, the positioning line 170 may be embedded into the couch 114. In some embodiments, the density of the positioning line 170 may be different from the density of the couch 114, so that the positioning line 170 may be distinguished from the couch 114 in an image including the positioning line 170 (or a portion thereof) and the couch 114 (or a portion thereof). For example, the positioning line 170 may include metal, for example, copper, iron, aluminum, or other metal with a low density (e.g., a density lower than a threshold density), or any combination thereof.

The positioning line 170 may have any suitable shape and/or size. In some embodiments, different portions of the positioning line 170 may have a uniform diameter. Optionally, the diameter of the positioning line 170 may be within a predetermined range, so that it may be able to be identified by the imaging component 113 and/or the treatment component 116. For example, the diameter of the positioning line 170 may be in a range from 0.2 millimeters (mm) to 1 mm, 0.5 mm to 1 mm, 1 mm to 2 mm, 3 mm to 5 mm, or the like. In some embodiments, the diameter of the positioning line 170 may be equal to 0.5 mm, 1 mm, 2 mm, 3 mm, 4 mm, or the like. In some embodiments, the positioning line 170 may cover a field of view (FOV) of the imaging component 113. As used herein, "cover an FOV" may refer to that a length of the positioning line 170 along the Y-axis direction in the coordinate system 160 is equal to or greater than a length of the FOV along the Y-axis direction. For example, if the length of the FOV along the Y-axis direction is 900 mm, the length of the positioning line 170 along the Y-axis direction may be equal to any value greater than 900 mm, for example, 1000 mm, 1100 mm, 1200 mm, 1500 mm, and so on.

In some embodiments, the positioning line 170 may have a specific shape (e.g., an N-shape, an S-shape, a V-shape, a W-shape, an irregular shape, a triangle, a trapezoid, a polygon), such that that the positioning line 170 may have a positioning feature. The positioning feature may have a plurality of unique feature values, each of which may correspond to a unique cross section of the couch 114. As used herein, a cross section of the couch 114 may refer to a cross section that is at an oblique angle with (e.g., perpendicular to) the Y-axis direction and a surface of the couch 114 on which the subject lies. Such positioning line 170 with a positioning feature may provide spatial and/or location information of the couch 114 and the subject lies on the couch 114. For example, the positioning line 170 may be used to determine a treatment position of the subject in a treatment session of the subject. More descriptions regarding the determination of a treatment position of a subject may be found elsewhere in the present disclosure. See, e.g., FIGS. 4A to 8 and relevant descriptions thereof.

For illustration purposes, a positioning line 170 having an N-shape as shown in FIG. 1 is taken as an example hereinafter. It should be understood that this is not intended to limit the scope of the present disclosure. The positioning line 170 may have any other shape that makes the positioning line 170 has a positioning feature, for example, an A-shape, an S-shape, a V-shape, a W-shape, a triangle, a trapezoid, a polygon, an irregular shape, or the like. For the positioning line 170 having an N-shape, a particular cross section of the couch may form an intersection with the N-shape positioning line 170. The intersection may include three points A, B, and C of the positioning line 170, wherein the point B may be located between the points A and C. Exemplary positioning features of the positioning line 170 may include the coordinates (e.g., X coordinates in the coordinate system 160) of points A and B in combination, the coordinates of points B and C in combination, the coordinates of points A, B, and C in combination, a distance between the points A and B (represented as IABI), a distance between the points B and C (represented as IBCI), a ratio of IABI to IBCI, a ratio of ICBI to IABI, a difference between IABI and IBCI, or the like, or any combination thereof.

In some embodiments, the couch 114 may include one or more fiducial markers. A fiducial marker may be placed at any position on the couch 114 that is visible to, e.g., the imaging component 113. A fiducial marker may be of any shape and/or size. For example, a plurality of fiducial markers may be placed near an edge of the couch 114. In some embodiments, a fiducial marker may have a known relative position with respect to, for example, the couch 114 and/or the positioning line 170. In some embodiments, the fiducial marker(s) may be used in determining a position of the positioning line 170. For example, the positions of a fiducial marker with respect to the radiation isocenter may be determined based on an image including the couch 114 acquired using the treatment radiation source 117 of the treatment component 116. A position of the positioning line 170 with respect to the radiation isocenter may be determined based on the position of the fiducial marker with respect to the radiation isocenter and the relative position of the fiducial marker with respect to the positioning line 170.

The network 120 may include any suitable network that can facilitate the exchange of information and/or data for the RT system 100. In some embodiments, one or more components of the RT system 100 (e.g., the radiation delivery device 110, the terminal(s) 130, the processing device 140, the storage device 150, etc.) may communicate information and/or data with one or more other components of the RT system 100 via the network 120. For example, the processing device 140 may obtain image data from the radiation delivery device 110 via the network 120. As another example, the processing device 140 may obtain user instructions from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
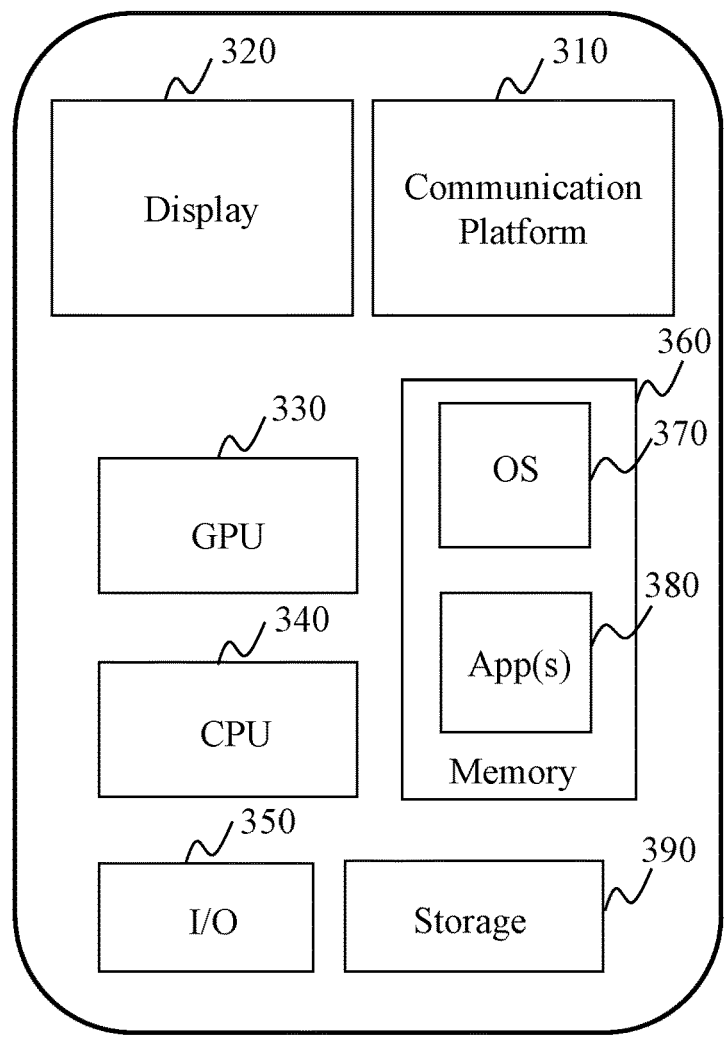
FIG. 3 is a schematic diagram illustrating exemplary hardware and/or software components of a mobile device according to some embodiments of the present disclosure.

The terminal(s) 130 may enable user interaction between a user and the RT system 100. In some embodiments, the terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process information obtained from the radiation delivery device 110, the terminal(s) 130, and/or the storage device 150. For example, the processing device 140 may determine a treatment position of the subject to be treated by analyzing an image of the subject acquired using the treatment component 116 and a treatment image of the subject acquired using the imaging component 113. In some embodiments, the processing device 140 may be a computer, a user console, a single server, a server group, etc. The server group may be centralized or distributed. In some embodiments, the processing device 140 may be local or remote. For example, the processing device 140 may access information stored in the radiation delivery device 110, the terminal(s) 130, and/or the storage device 150 via the network 120. As another example, the processing device 140 may be directly connected to the radiation delivery device 110, the terminal(s) 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the RT system 100 (e.g., the processing device 140, the terminal(s) 130). One or more components of the RT system 100 may access the data and/or instructions stored in the storage device 150 via the network 120. In some embodiments, the storage device 150 may be directly connected to or communicate with one or more other components of the RT system 100 (e.g., the processing device 140, the terminal(s) 130). In some embodiments, the storage device 150 may be part of the processing device 140. In some embodiments, the storage device 150 may be connected to or communicate with the radiation delivery device 110 via the network 120, or at the backend of the processing device 140.

In some embodiments, a coordinate system may be provided for the RT system 100 to define a position of a component (e.g., an absolute position, a position relative to another component) and/or a movement of the component. For illustration purposes, an International Electrotechnical Commission (IEC) coordinate system 160 is provided in FIG. 1. The IEC coordinate system 160 may be a right-handed Cartesian system including an X-axis, the Y-axis, and a Z-axis. The X-axis and the Y-axis shown in FIG. 1 may be horizontal, and the Z-axis may be vertical. The origin of the coordinate system 160 may be located at the isocenter of the LINAC of the treatment component 116. As illustrated, the positive X direction along the X-axis may be from the left side to the right side of the couch 114 viewed from the direction facing the front of the radiation delivery device 110; the positive Y direction along the Y-axis shown in FIG. 1 may be from the end to the head of the couch 114; the positive Z direction along the Z-axis shown in FIG. 1 may be from the lower part to the upper part of the gantry 118.

It should be noted that the provided coordinate system 160 is illustrative, and not intended to limit the scope of the present disclosure. For example, the origin of the coordinate system 160 may be located at any other position (e.g., the rotation center of the gantry 111 of the imaging component 113, thus forming a coordinate system with respect to the imaging component 113). As another example, the coordinate system 160 may only include two axes (e.g., the X-axis and the Y-axis). In addition, although the following descriptions discuss through various examples to determine a position of an entity by determining a coordinate of an entity in a certain coordinate system, it should be understood that the position of the entity may be determined by determining a coordinate of the entity in another coordinate system (e.g., a coordinate system that has a known transformation relationship with the certain coordinate system). For the convenience of descriptions, coordinates of an entity along an X-axis, a Y-axis, and a Z-axis in a coordinate system are also referred to as an X-coordinate, a Y-coordinate, and Z-coordinate of the entity in the coordinate system, respectively.

It should be noted that the above description regarding the RT system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the RT system 100 may include one or more additional components and/or one or more components of the RT system 100 described above may be omitted. Additionally or alternatively, two or more components of the RT system 100 may be integrated into a single component. A component of the RT system 100 may be implemented on two or more sub-components.

FIG. 2 is a schematic diagram illustrating exemplary hardware and/or software components of a computing device 200 according to some embodiments of the present disclosure. The computing device 200 may be used to implement any component of the RT system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the RT system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the radiation delivery device 110, the terminal(s) 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data obtained from one or more components of the RT system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 to execute to check errors in replanning.

The I/O 230 may input and/or output signals, data, information, etc. In some embodiments, the I/O 230 may enable user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the radiation delivery device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of a mobile device 300 according to some embodiments of the present disclosure. In some embodiments, a terminal(s) 130 and/or a processing device 140 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
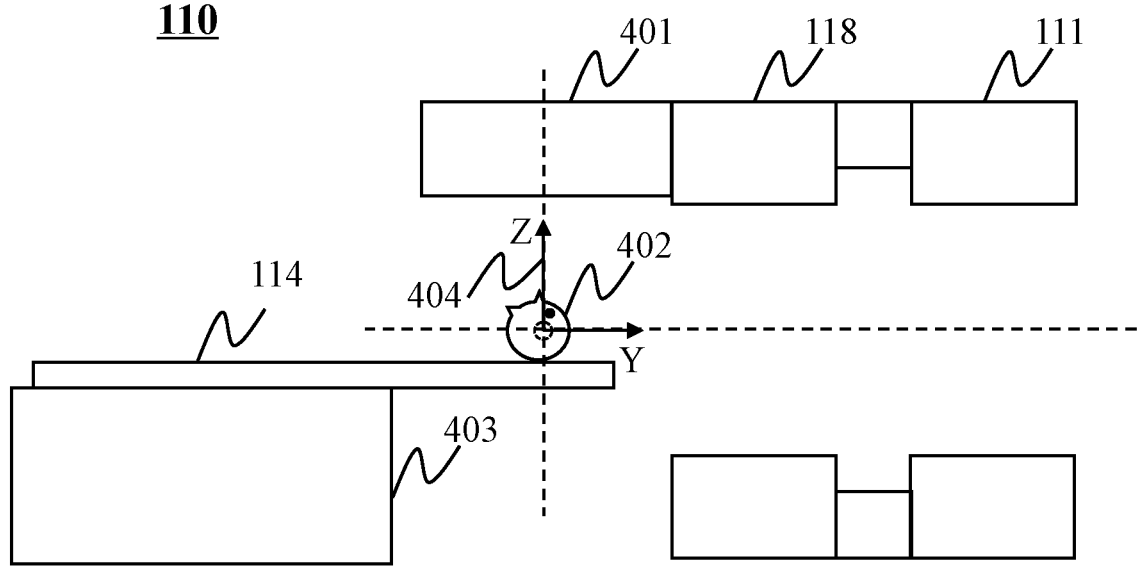
FIGS. 4A and 4B are schematic diagrams illustrating an exemplary radiation delivery device according to some embodiments of the present disclosure.
Figure 4B:
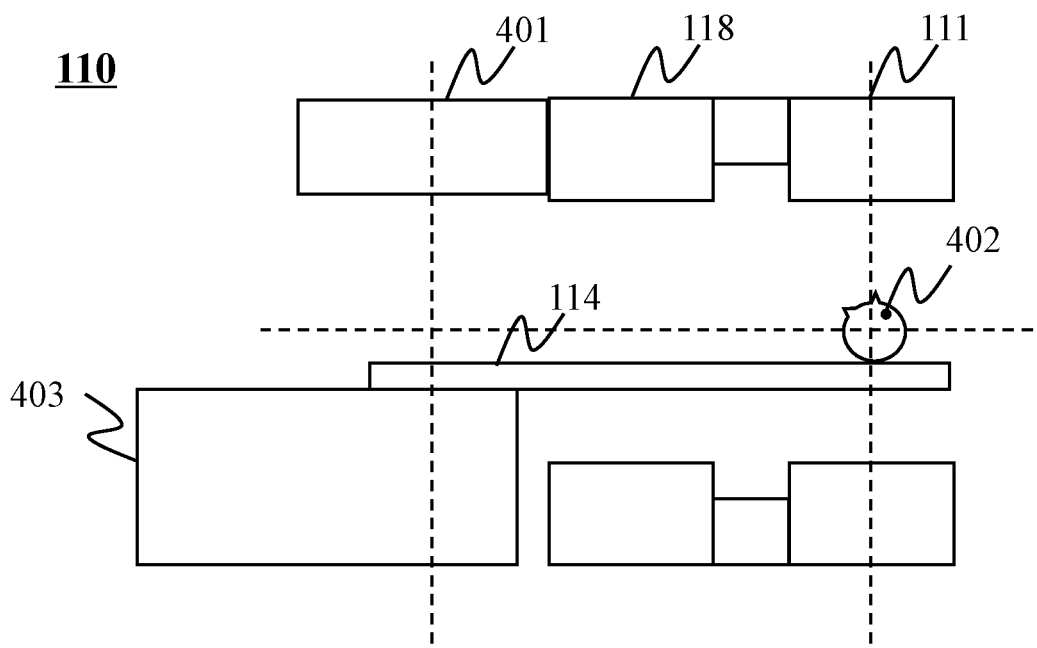

FIGS. 4A and 4B are schematic diagrams illustrating an exemplary radiation delivery device 110 according to some embodiments of the present disclosure. The radiation delivery device 110 may include a treatment component, an imaging component (e.g., a CT device), a couch 114, and a couch base 403. The treatment component may include a treatment radiation source 401 (e.g., an MV treatment source), a gantry 118, a collimator, a detector (e.g., placed opposite to the treatment radiation source 401 and not shown in figures), or the like, or any combination thereof. The imaging component may include a gantry 111, an imaging radiation source, a detector, or the like, or any combination thereof. The couch base 403 may be configured to support the couch 114.

In some embodiments, the treatment radiation source 401 may rotate around a rotation center (also be referred to as a radiation isocenter) during treatment. For example, the treatment radiation source 401 may include a LINAC, and the radiation isocenter of the treatment radiation source 401 may be a rotation isocenter of the LINAC. In some embodiments, a plane passing through the radiation isocenter and being perpendicular to a Y-axis of a coordinate system 404 may be referred to as an isocentric plane of the treatment radiation source 401 and be coincident with an X-Z plane defined by the coordinate system 404. The coordinate system 404 may be a same or a similar coordinate system as the IEC coordinate system 160 as described in connection with FIG. 1. The coordinate system 404 may include the Y-axis, a Z-axis, and an X-axis (which is perpendicular to the Y-Z plane formed by the Y-axis and the Z-axis and not shown in FIG. 4A). The origin of the coordinate system 404 may coincide with the radiation isocenter of the treatment radiation source 401.

In some embodiments, the radiation delivery device 110 may be used to deliver a radiotherapy treatment to the subject. The subject may include any biological subject and/or a non-biological subject. Exemplary biological subject may include a human being, an animal, a plant, or a portion thereof (e.g., a cell, a tissue, an organ, etc.). In some embodiments, the subject may include a target 402. The target 402 may include a region of the subject including at least part of malignant tissue (e.g., a tumor, a cancer-ridden organ, or a non-cancerous target of radiation therapy) and/or other tissue (e.g., a tissue surrounding the malignant tissue). For example, the target 402 may be a tumor, an organ with a tumor, a tissue with a tumor, or any combination thereof, that needs to be treated by radiations.

Conventionally, before the subject begins to receive the radiotherapy treatment (e.g., days or weeks before the treatment commences), a planning image (e.g., a CT image) of the subject may be acquired using the imaging component of the radiation delivery device 110 (or another imaging device). As used herein, a planning image may refer to an image according to which a treatment plan for the subject is made. The treatment plan may describe how the radiotherapy treatment is planned to be performed on the subject, more specifically, how one or more beams are delivered to the target 402 of the subject during each treatment session over the course of treatment lasting a certain period of time, e.g., days. For example, the treatment plan may provide a total dose (e.g., 0.1 Gy, 10 Gy, 50 Gy, 100 Gy, etc.) and a dose distribution in the target 402.

The treatment plan may be delivered to the subject during several treatment sessions, spread over a treatment period of multiple days (e.g., 2 to 5 weeks). However, during the treatment period, setup errors may appear, and an anatomical change (e.g., weight loss, growth, shrinkage, or disappearance of a tumor, the appearance of a new tumor, etc.) may take place within the subject. The size and/or position of a certain organ may change between the time of planning and the time of a treatment session. Therefore, every time the subject comes for a specific treatment session, to ensure accurate positioning of the subject for the execution of the specific treatment session, the subject may be scanned for generating a treatment image. The treatment image may refer to an image of the subject captured during the treatment procedure, for example, right before (e.g., minutes or hours before) the current treatment session starts or during the current treatment session. The anatomical change of the subject may be identified by comparing (e.g., registering) the planning image and the treatment image. A treatment position of the subject in the current treatment session may then be determined based on the comparison result between the planning image and the treatment image.

In some embodiments, the treatment image may be acquired using a non-in-suit imaging device, i.e., an imaging component like the one illustrated in FIGS. 4A and 4B which is spaced by a distance from the treatment component. In other words, in the treatment session, the subject may need to be moved between the imaging component and the treatment component via the couch 114 for imaging and treatment. For example, before the current session, the subject may be placed at a set-up position with respect to the treatment component by the couch 114 as shown in FIG. 4A. The set-up position may be closer to the treatment component and away from the imaging component, for example, under the treatment radiation source 401 of the treatment component. In some embodiments, the set-up position may be determined based on, for example, the treatment plan, the planning image, or a previous treatment image which is acquired in a previous treatment session of (e.g., a treatment session immediately before) the treatment session. For example, the subject may be placed at a set-up position such that the target 402 (e.g., an isocenter of the target 402 determined based on the planning image or the previous treatment image) may be located at or near the radiation isocenter of the treatment radiation source 401. In some embodiments, the subject may be placed at a fixed or approximately fixed position on the couch 114 during treatment. A certain position (e.g., the set-up position, a treatment position, and/or an imaging position disclosed herein) of the subject may be represented by a corresponding position (e.g., an encoder position) of the couch 114 when the subject is at the certain position. Merely by way of example, the set-up position may be represented by a known encoder position of the couch 114 measured by a position encoder of the couch 114.

After being set-up, the subject may be moved from the set-up position to a planned imaging position with respect to the imaging component via the couch 114 for acquiring a treatment image. For example, the couch 114 may move from the position as shown in FIG. 4A to a position as shown in FIG. 4B along the Y-axis direction of the coordinate system 404. When the couch 114 is located at the position as shown in FIG. 4B, the subject may be located at the imaging position with respect to the imaging component (e.g., under the imaging radiation source of the imaging component). In some embodiments, the target 402 may be located at or near the rotation center of the gantry 111 of the imaging component when the subject is at the imaging position during the acquisition of the treatment image.

In the cases that the treatment image is acquired using a non-in-situ imaging device, a treatment position, which may align a treatment isocenter identified from the treatment image with the radiation isocenter, may need to be determined. In some embodiments, the couch 114 may include a positioning line (e.g., an N-shape positioning line) disclosed herein. Conventionally, the treatment position may be determined by performing a calibration of the positioning line. For example, in the treatment image, an image plane that passes through a treatment isocenter and an intersection of the positioning line with the image plane may be determined. A relative position of the treatment isocenter with respect to the intersection may be determined. A calibration of the positioning line may be performed to determine that at different encoder positions of the couch, what is the intersection of the positioning line with the radiation plane and a relative position of the intersection with respect to the radiation isocenter. The treatment position may be determined based on the calibration and the relative position of the treatment isocenter with respect to the intersection identified in the treatment image. However, the calibration of the positioning line may be time-consuming and need the intervention of an operator (e.g., a doctor) of the radiation delivery device 110.

To obviate the need for calibration and/or improve the positioning precision, it is desirable to provide an effective mechanism for treatment positioning. As aforementioned, the subject may be positioned at a set-up position as illustrated in FIG. 4A before a current treatment session. The treatment radiation source 401 may be used to perform a scan (e.g., a tomographic imaging) of the subject at the set-up position, wherein a resulting image of the scan may be used to determine a first position of the radiation isocenter with respect to the positioning line during the scan. Based on the treatment image acquired at the imaging position, a second position of the treatment isocenter of the subject with respect to the positioning line during the acquisition of the treatment image may be determined. Based on the first position and the second position, the treatment position may be determined. More descriptions regarding the determination of the treatment position may be found elsewhere in the present disclosure. See, e.g., FIGS. 5 to 8 and relevant descriptions thereof.

It should be noted that the above descriptions of the radiation delivery device 110 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the radiation delivery device 110 may include one or more other components and/or one or more components described above may be omitted. For example, the treatment component may include an additional radiation source (e.g., a KV radiation source) other than the treatment radiation source 401 to image the subject at the set-up position. However, those variations and modifications also fall within the scope of the present disclosure.

Figure 5:
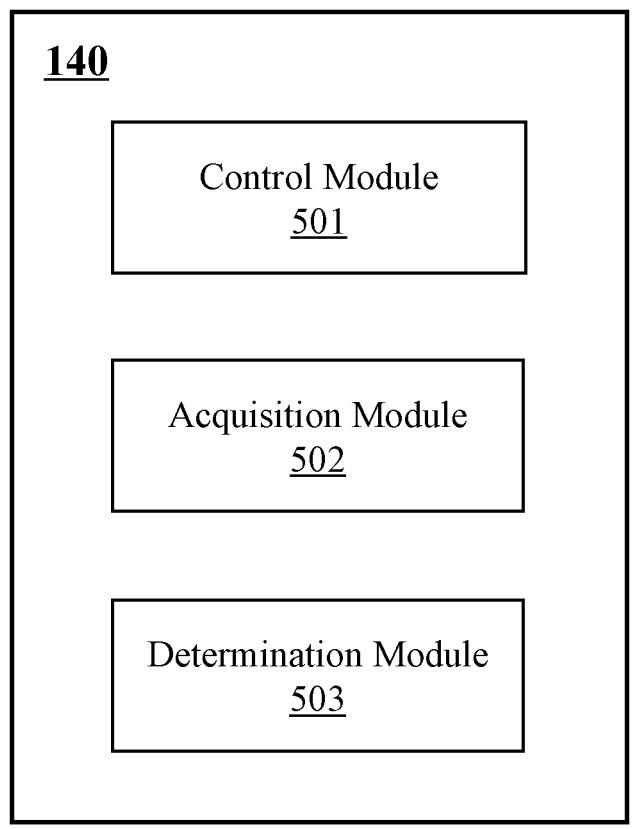
FIG. 5 is a block diagram illustrating an exemplary processing device according to some embodiments of the present disclosure.

FIG. 5 is a block diagram illustrating an exemplary processing device 140 according to some embodiments of the present disclosure. As shown in FIG. 5, the processing device 140 may include a control module 501, an acquisition module 502, and a determination module 503.

The control module 501 may be configured to control one or more components of the RT system 100. For example, the control module 501 may cause the couch 114 to move a subject lying on the couch 114 from a set-up position to an image position for imaging. As another example, the control module 501 may cause the couch 114 to move the subject from the image position to a treatment position for treatment. In some embodiments, the control module 501 may control a component of the RT system 100 by transmitting an instruction to the component. More descriptions regarding the set-up position, the imagining position, and the treatment position may be found elsewhere in the present closure. See, e.g., FIGS. 4 and 6 and the descriptions thereof.

The acquisition module 502 may be configured to acquire information relating to the RT system 100. In some embodiments, the acquisition module 502 may acquire one or more images of the subject from one or more components of the RT system 100. For example, the acquisition module 502 may acquire one or more first images of the subject. The first image(s) may be acquired (or captured) using a radiation source (e.g., a MV treatment source, or a KV radiation source) of the treatment component 116 when the subject is located at the set-up position. As another example, the acquisition module 502 may acquire one or more treatment images (also referred to as second images) of the subject. The treatment image(s) may be acquired (or captured) using the imaging component 113 when the subject is located at the imaging position. In some embodiments, an image of the subject may be obtained from a computing device (e.g., the processing device 140) that reconstructs the image, a storage device that stores the image, a device that acquires (or captures) the image, or the like. More descriptions regarding the first image(s) and the treatment image(s) may be found elsewhere in the present closure. See, e.g., FIG. 6 and the descriptions thereof.

The determination module 503 may be configured to determine a treatment isocenter of a target (e.g., a tumor) of the subject based on the treatment image(s) according to one or more image analysis algorithms (e.g., an image segmentation algorithm, an image registration algorithm). The treatment isocenter may refer to an isocenter (e.g., a central point) of the target. As another example, the determination module 503 may determine the treatment position of the subject based on the first image(s), the treatment image(s), and the positioning line 170. More descriptions regarding the determination of the treatment isocenter and the treatment position may be found elsewhere in the present disclosure. See. e.g., FIGS. 6 and 8 and the descriptions thereof.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. Additionally or alternatively, two or more modules may be integrated into a single module and/or a module may be divided into two or more units. However, those variations and modifications also fall within the scope of the present disclosure.

Figure 6:
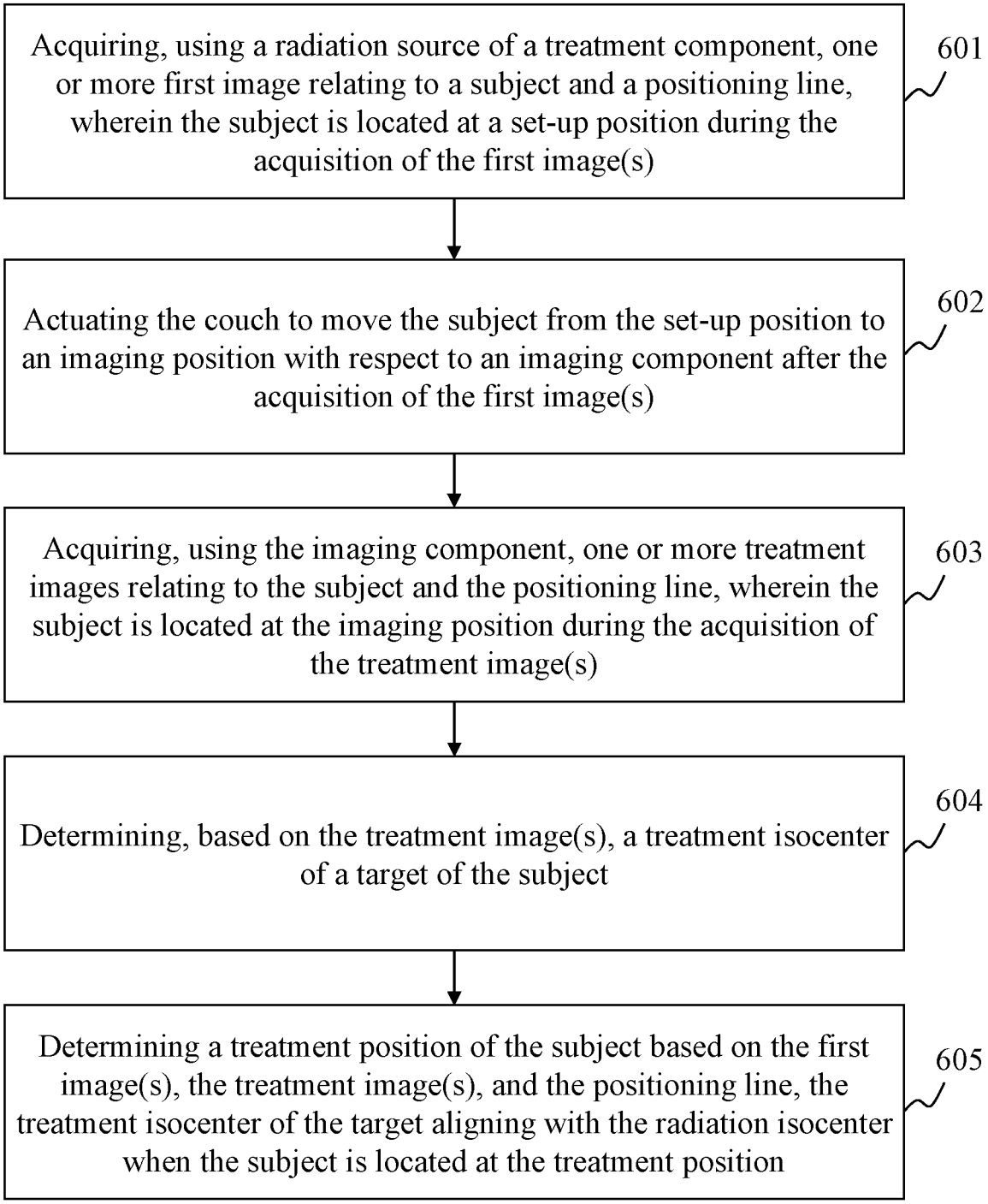
FIG. 6 is a flowchart illustrating an exemplary process for determining a treatment position of a subject according to some embodiments of the present disclosure.

FIG. 6 is a flowchart illustrating an exemplary process for determining a treatment position of a subject according to some embodiments of the present disclosure. In some embodiments, process 600 may be executed by the RT system 100. For example, the process 600 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 6) may execute the set of instructions and may accordingly be directed to perform the process 600.

In some embodiments, a radiation delivery device (e.g., the radiation delivery device 110) may be used to perform a radiotherapy treatment on the subject (e.g., a patient, a portion of the patient, a man-made object, etc.). The radiation delivery device may include a treatment component (e.g., the treatment component 116), an imaging component (e.g., the imaging component 113), and a couch (e.g., the couch 114) including a positioning line (e.g., the positioning line 170). For illustration purposes, the following descriptions are described with reference to an N-shape positioning line, and not intended to limit the scope of the present disclosure. The treatment component may include a radiation source that has a radiation isocenter (i.e., a rotation center of the radiation source). In some embodiments, the radiation source may be a treatment radiation source (e.g., an MV treatment source) of the treatment component. Alternatively, the treatment component may include an additional radiation source (e.g., a KV radiation source) other than the treatment radiation source, wherein the radiation isocenter of the additional radiation source may coincide with the radiation isocenter of the treatment radiation source 117. The radiation source may be the additional radiation source other than the treatment radiation source. The couch may be configured to support the subject and movable between the treatment component and the imaging component along a Y-axis direction (or referred as a reference axis) (e.g., the Y-axis of the coordinate system 404 or the coordinate system 160).

As described elsewhere in this disclosure, the radiotherapy treatment may include a plurality of treatment sessions and last for a treatment period of multiple days (e.g., 2 to 5 weeks). For illustration purposes, an implementation of a current treatment session by the radiation delivery device is described hereinafter. Before the current treatment session, the subject may be placed at a set-up position via the couch. For example, the subject may be placed at a set-up position adjacent to the treatment component and away from the imaging component as illustrated in FIG. 4A. In some embodiments, the set-up position may be determined based on the treatment plan or an image (e.g., a planning image, a previous treatment image) of the subject which is acquired prior to the current treatment session. For example, a set-up position at which the target (e.g., an isocenter of the target) of the subject aligns the radiation isocenter may be determined based on the image. In some embodiments, a marker (e.g., a fiducial marker) may be placed inside the target or on the body surface near the target of the subject. The subject may be moved to the set-up position via the couch by aligning the marker with the radiation isocenter.

In 601, the processing device 140 (e.g., the acquisition module 502) may acquire one or more first images relating to the subject and the positioning line using the radiation source of the treatment component. The subject may be located at the set-up position during the acquisition of the at least one first image.

In some embodiments, the first image(s) may include one or more 2D images acquired using the radiation isocenter.

Figure 7:
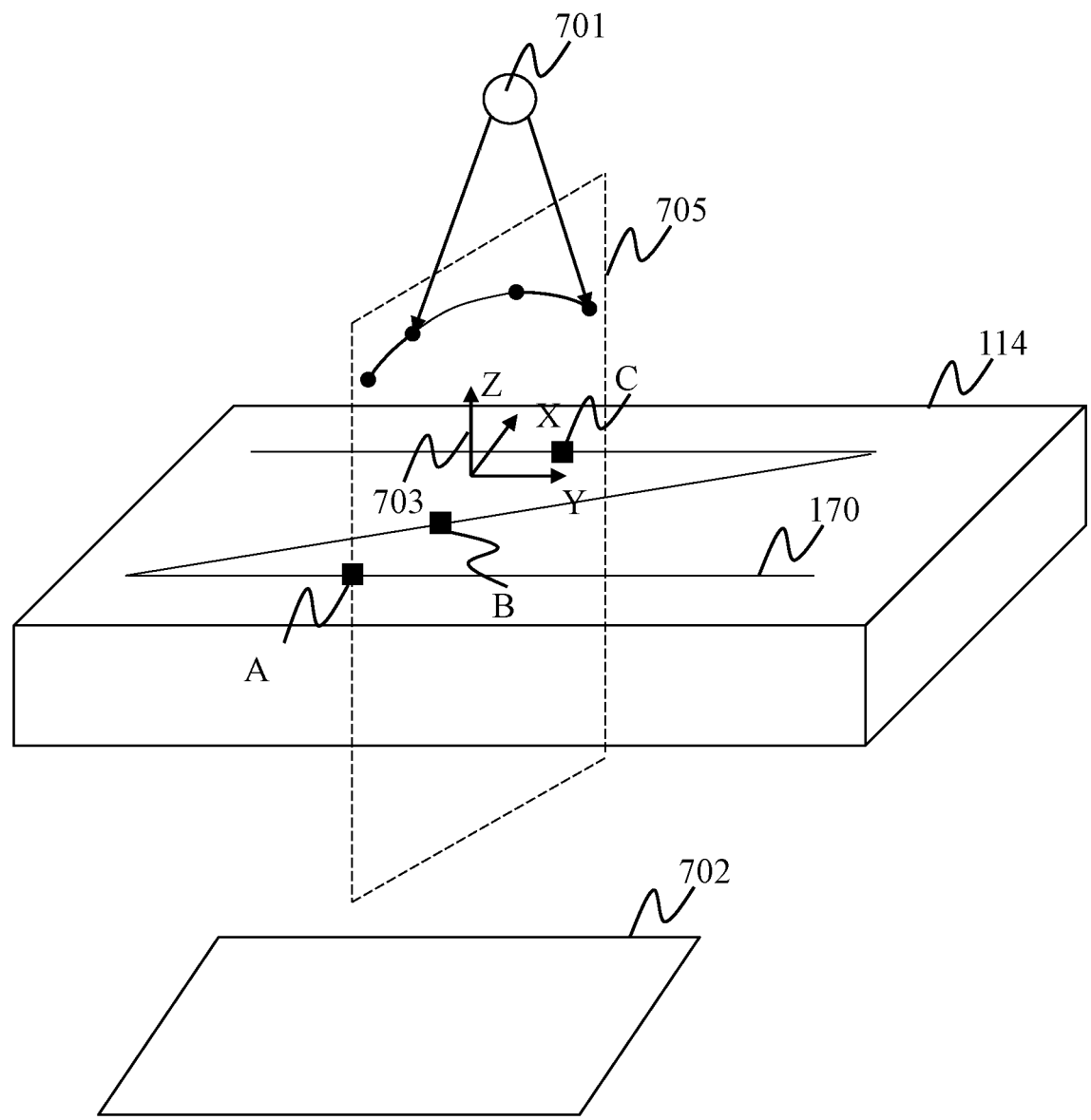
FIG. 7 is a schematic diagram of an exemplary process for acquiring at least one first image of a subject using a radiation source of a radiation delivery device according to some embodiments of the present disclosure.

For illustration purposes, FIG. 7 illustrates a schematic diagram of an exemplary process for acquiring the first image(s) using a radiation source 701 of a radiation delivery device according to some embodiments of the present disclosure. The radiation isocenter of the radiation source 701 may coincide with the origin of a coordinate system 703 as illustrated in FIG. 7. The coordinate system 703 may be the same as or similar to the coordinate system 404 described in FIG. 4A. The Y-axis of the coordinate system 703 may be parallel with the moving direction of the couch 114 (i.e., the reference axis described above). An isocentric plane 705 of the radiation source 701 may coincide with the X-Z plane defined by the coordinate system 703. In some embodiments, the isocentric plane 705 and the positioning line 170 may form a first intersection. The first intersection may include a first intersection point A, a first intersection point B, and a first intersection point C as shown in FIG. 7.

As shown in FIG. 7, the radiation source 701 may rotate around its radiation isocenter on the isocentric plane 705 to move to different positions. At each position, the radiation source 701 may be configured to perform a tomographic scan on the subject, and a detector 702 (e.g., an electronic portal imaging device (EPID)) may be configured to acquire image data of the subject during the tomographic scan. The image data acquired by the detector 702 in each tomographic scan may be used to reconstruct a 2D projection (i.e., a 2D first image) relating to the first intersection and an intersection of the subject with the isocentric plane 705. A reconstructed 2D projection may include a representation of the radiation isocenter, the isocentric plane 705, the Y-axis, the positioning line 170, the subject, or the like, or any combination thereof. For example, a 2D projection may include a point representing a projection of the radiation isocenter, a line representing a projection of the isocentric plane 705, a line representing a projection of the Y-axis, three lines representing a projection of the N-shape positioning line 170 (or a portion thereof), three points representing projections of the first intersection (e.g., three points representing projections of the first intersection points A, B, and C), or the like, or any combination thereof.

In some embodiments, the radiation source 701 may be configured to perform a limited angle tomographic scan on the subject to generate a plurality of 2D projections. In the limited angle tomographic scan, the radiation source 701 may rotate in a limited range of projection angles and scan the subject at certain projection angles. For example, a projection angle of the radiation source 701 may refer to an angle between a line connecting the radiation source 701 and the radiation isocenter and a certain direction (e.g., the Z-axis direction of the coordinate system 703). The limited range of the projection angles may be, for example, [−10°, 10°], [−15°, 15°], [−30°, 30°]. In some embodiments, the radiation source 701 may scan the subject in every fixed change (e.g., 3 degrees, 5 degrees, 10 degrees, etc.,) in the projection angle. For example, the projection angle may range from −15° to 15° and the radiation source 701 may scan the subject in every 10° change in projection angle, thereby generating four 2D projections.

In 602, the processing device 140 (e.g., the control module 501) may cause the couch to move the subject from the set-up position to the imaging position with respect to the imaging component after the acquisition of the first image(s).

The imaging position may refer to a position at which the subject may be imaged for generating a treatment image (or referred to as a second image) by the imaging component. In some embodiments, the couch may move along a moving path to reach to the imaging position. The moving path may be parallel with or substantially parallel with the Y-axis as described above.

In 603, the processing device 140 (e.g., the acquisition module 502) may acquire one or more treatment images relating to the subject and the positioning line using the imaging component. The subject may be located at the imaging position during the acquisition of the treatment image.

In some embodiments, the treatment image may be a three-dimensional (3D) image relating to the subject and the positioning line. Alternatively, the treatment image may include a plurality of 2D images (e.g., slice images) relating to the subject and the positioning line, wherein the combination of the 2D images may be regarded as a 3D image of the subject. In some embodiments, the processing device 140 may direct the imaging component to perform a scan (e.g., an FBCT scan) on the subject to acquire scan data of the subject. The FOV of the imaging component during the scan may cover the subject and the at least a portion of the positioning line. The processing device 140 may reconstruct the treatment image based on the scan data.

Alternatively, the processing device 140 may acquire the treatment image from another computing device that reconstructs the treatment image or a storage device (e.g., the storage device 150, the storage 220, an external source) that stores the treatment image.

In 604, the processing device 140 (e.g., the determination module 503) may determine a treatment isocenter of a target (e.g., a tumor) of the subject based on the treatment image(s).

The treatment isocenter may refer to an isocenter (e.g., a central point) of the target. In some embodiments, the processing device 140 may determine the treatment isocenter based on the treatment image according to one or more image analysis algorithms (e.g., an image segmentation algorithm). Merely by way of example, the treatment isocenter may be determined by registering the treatment image with a planning image of the subject. The planning image may be acquired using the imaging component of the radiation delivery device (or another imaging device) prior to the treatment image, for example, before the subject begins to receive the radiotherapy treatment (e.g., days or weeks before the radiotherapy treatment commences). A planning isocenter (i.e., a center point of the target at the time when the planning image is acquired) may be previously identified in the planning image. The processing device 140 may determine the treatment isocenter in the treatment image based on the planning isocenter and a registration result between the treatment image and the planning image. In some embodiments, in the treatment image(s), the processing device 140 may identify an image plane that passes through the treatment isocenter and is perpendicular to the Y-axis direction, and a second intersection between the image plane and the positioning line for further analysis as described elsewhere in this disclosure (e.g., FIG. 8 and the relevant descriptions).

In 605, the processing device 140 (e.g., the determination module 503) may determine a treatment position of the subject based on the first image(s), the treatment image(s), and the positioning line. The treatment isocenter of the target may align with the radiation isocenter when the subject is located at the treatment position. Additionally or alternatively, the second intersection of the positioning line may coincide with the isocentric plane of the treatment component when the subject is located at the treatment position.

In some embodiments, based on the first image(s), the processing device 140 may determine a first position of the radiation isocenter relative to the positioning line when the subject is at the set-up position (i.e., during the acquisition of the first image(s)). Based on the treatment image(s), the processing device 140 may determine a second position of the treatment isocenter relative to the positioning line when the subject is at the imaging position (i.e., during the acquisition of the treatment image(s)). Further, the processing device 140 may determine the treatment position at which the radiation isocenter aligns with the treatment isocenter of the subject and/or the second intersection coincides with the isocentric plane based on the first and second positions. For example, an offset (e.g., offsets along the X-axis direction, the Y-axis direction, and/or the Z-axis direction in the coordinate system 703, an angular deviation of the couch) between the treatment position and the set-up position may be determined based on the first and second positions. The treatment position may be determined to compensate for the offset between the treatment position and the set-up position. In some embodiments, the processing device 140 may determine the treatment position by performing one or more operations of process 800 as described in connection with FIG. 8.

In some embodiments, after the treatment image is acquired, the processing device 140 may cause the couch to move the subject from the imaging position back to the set-up position. The processing device 140 may further cause the couch to move the subject from the set-up position to the treatment position to remove the offset of the treatment position with respect to the set-up position. Alternatively, the processing device 140 may cause the couch to move the subject from the imaging position to the treatment position directly. Optionally, the current treatment session may be delivered to the subject by the treatment component after the subject is moved to the treatment position.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. Additionally, the order of the process 600 may not be intended to be limiting.

Figure 8:
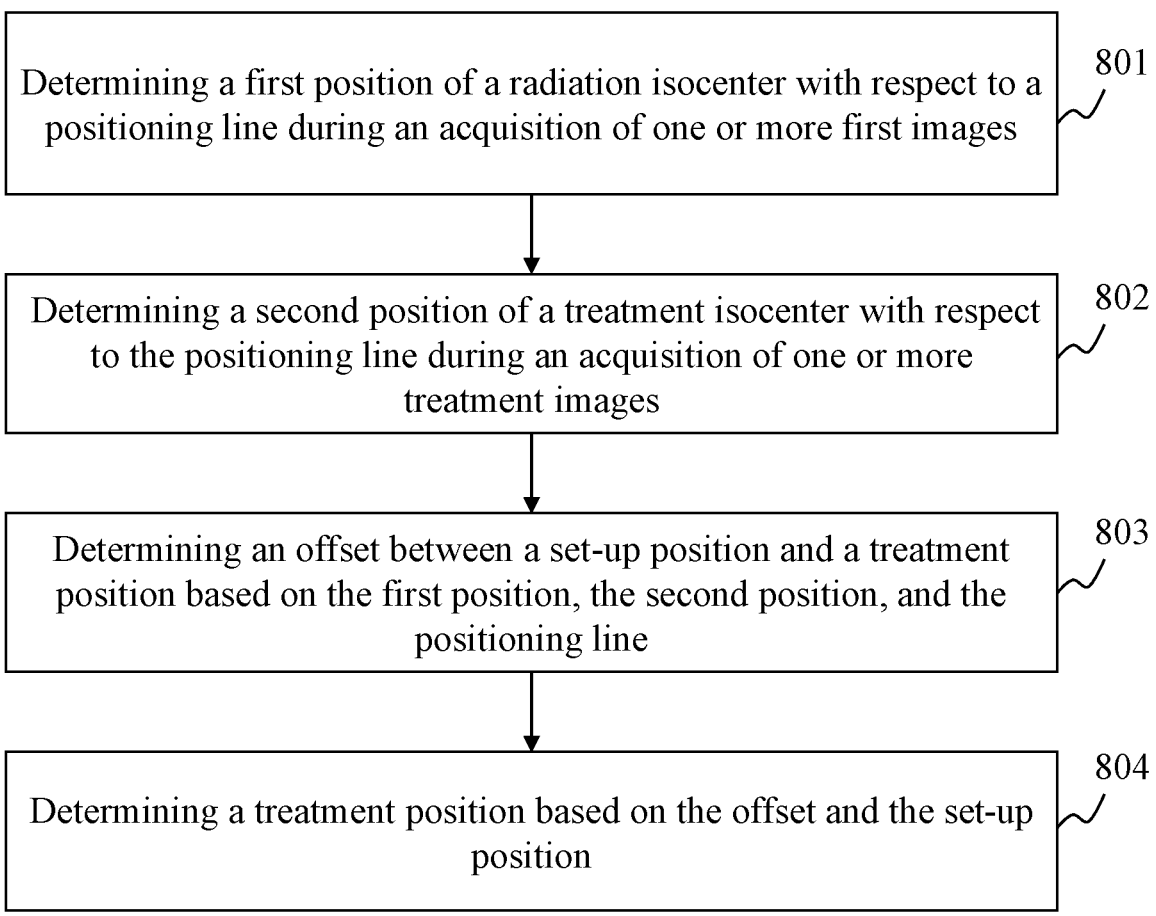
FIG. 8 is a flowchart illustrating an exemplary process for determining a treatment position of a subject according to some embodiments of the present disclosure.

FIG. 8 is a flowchart illustrating an exemplary process for determining a treatment position of a subject according to some embodiments of the present disclosure. In some embodiments, process 800 may be executed by the RT system 100. For example, the process 800 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 6) may execute the set of instructions and may accordingly be directed to perform the process 800. In some embodiments, one or more operations of the process 800 may be performed to achieve at least part of operation 605 as described in connection with FIG. 6.

In 801, the processing device 140 (e.g., the determination module 503) may determine a first position of the radiation isocenter with respect to the positioning line during an acquisition of the first image(s) based on the first image(s) (i.e., when the subject is at the set-up position).

In some embodiments, the first image(s) may include a plurality of 2D projections relating to a first intersection between the positioning line and the isocentric plane (e.g., the X-Z plane defined by the coordinate system 703) as described in connection with FIGS. 6 and 7. The first position of the radiation isocenter with respect to the positioning line may be represented by a position of the radiation isocenter with respect to the first intersection. For example, the first intersection may include three first intersection points (e.g., points A, B, and C as shown in FIG. 7). The first position may include a vertical distance (i.e., a distance along the Z-axis direction) between the radiation isocenter and each first intersection point, an average value of the vertical distances between the radiation isocenter and the first intersection points, a horizontal distance (i.e., a distance along the X-axis direction) between the radiation isocenter and each first intersection point, an average value of the horizontal distances between the radiation isocenter and the first intersection points, or the like, or any combination thereof.

In some embodiments, the processing device 140 may determine coordinate(s) of one or more of the first intersection points based on the 2D projections. For a certain first intersection point, the processing device 140 may determine a position of the radiation isocenter relative to the certain first intersection point based on the coordinates of the radiation isocenter and the certain intersection point. For example, the first intersection points may have unknown 3D coordinates (x1, y1, z1), (x2, y2, z2), and (x3, y3, z3) in the coordinate system 703, respectively. An $i^{th}$ 2D projection may correspond to a 2D projection system and a calibrated projection matrix $P_i$. The calibrated projection matrix $P_i$ may be configured to transform a 3D coordinate in the coordinate system 703 to a 2D coordinate in the 2D projection system of the $i^{th}$ 2D projection. The 2D coordinates of the projection of the first intersection points in the 2D projection system may be expressed based on the calibrated projection matrix $P_i$ and the 3D coordinates of the first intersection points according to Equations (1) to (3), respectively:

$$(u1, v1)_i = (x1, y1, z1) \times P_i, \quad (1)$$

$$(u2, v2)_i = (x2, y2, z2) \times P_i, \quad (2)$$

$$(u3, v3)_i = (x3, y3, z3) \times P_i, \quad (3)$$

where, $(u1, v1)_i$, $(u2, v2)_i$, and $(u3, v3)_i$ may represent 2D coordinates of the projections of the first intersection points, respectively. The processing device 140 may determine the 3D coordinates of the first intersection points based on a plurality sets of equations corresponding to the plurality of 2D projections. The coordinates of the first intersection points may indicate an exact position of the N-shape positioning line in the coordinate system 703 when the subject is at the set-up position. The processing device 140 may also determine a position of the radiation isocenter with respect to the first intersection by determining a position of the radiation isocenter with respect to the first intersection points (or a portion thereof) based on their respective coordinates in the coordinate system 703.

Additionally or alternatively, the first position of the radiation isocenter with respect to the positioning line may be represented by an angular orientation of the positioning line at the set-up position. The angular orientation of the positioning line may be measured by, for example, an angle between one of the two parallel arms of the N-shape positioning line and a reference system (e.g., the Y-axis, the isocentric plane). The angular orientation of the positioning line may represent an angular orientation of the couch. In some embodiments, the first image(s) may include one or more 2D projections, and the angular orientation of the positioning line may be determined based on one of the 2D projection(s). For example, based on the projection of the Y-axis (e.g., a line) and the projection of the two parallel arms of the N-shape positioning line (e.g., two parallel lines) in a 2D projection, the processing device 140 may determine an angle between one of the parallel arms and the Y-axis as the angular orientation of the positioning line. Alternatively, the processing device 140 may determine angles between the Y-axis and one of the parallel arms of the positioning line in more than one 2D projections, and determine the angular orientation of the positioning line by determining, e.g., an average of the angles.

In 802, the processing device 140 (e.g., the determination module 503) may determine a second position of a treatment isocenter with respect to the positioning line during an acquisition of the treatment image(s) based on the treatment image(s) (i.e., when the subject is at the imaging position).

In some embodiments, the treatment image(s) may include a 3D image of the subject (e.g., one 3D image or a combination of a plurality of slice images) as described in connection with FIG. 6. The processing device 140 may identify an image plane that passes through the treatment isocenter of the subject and is perpendicular to the Y-axis in the 3D image of the subject. The processing device 140 may further determine a second intersection between the image plane and the positioning line based on the 3D image. The processing device 140 may then determine the second position of the treatment isocenter with respect to the positioning line by determining a position of the treatment isocenter with respect to the second intersection. In some embodiments, similar to the first intersection as aforementioned, the second intersection may include three second intersection points between the positioning line and the image plane. The position of the treatment isocenter with respect to the second intersection may include a position of the treatment isocenter with respect to one or more of the second intersection points and/or an angular orientation of the positioning line at the imaging position.

In 803, the processing device 140 (e.g., the determination module 603) may determine an offset between the set-up position and the treatment position (denoted by $O_1$) based on the first position, the second position, and the positioning line.

As used herein, an offset between the two positions may include a vertical offset along the Z-axis direction, a longitudinal offset along the Y-axis direction, a horizontal offset along the X-axis direction, or the like, or any combination thereof, between the two positions. Additionally or alternatively, the offset between the two positions may include an angular deviation (i.e., a difference in the angular orientation) of the positioning line (or the couch) at the two positions. The offset $O_1$ may need to be compensated for so that, when the subject is at the treatment position, the treatment isocenter may align with the radiation isocenter and/or the second intersection of the positioning line may align with the isocentric plane. In some embodiments, the offset $O_1$ may only include an angular deviation of the positioning line at the set-up position and the treatment position (e.g., if only one first image is acquired in 601). The angular deviation may need to be removed so that, when the subject is at the treatment position, the second intersection of the positioning line aligns with the isocentric plane. In such cases, the radiation isocenter and the treatment isocenter may be regarded as being aligning with each other if the angular deviation is removed.

In some embodiments, the subject may need to be moved back to the set-up position after the acquisition of the treatment image via the couch. It is assumed in the present disclosure that the movement from the setup position to the imaging position and back to the setup position is repeatable. The offset $O_1$ may be determined by determining an offset between the radiation isocenter and the treatment isocenter when the subject is moved back to the set-up position (denoted as $O_2$). After the subject is moved back to the set-up position, the positioning line (or the couch) may be located at a same or substantially same location as that during the acquisition of the first image(s). The offset $O_2$ may be determined by taking the positioning line (or the couch) as a reference substance. Merely by way of example, when the subject is moved back to the set-up position, a relative position between the first intersection and the second intersection of the positioning line may be determined. The offset $O_2$ may be determined based on the relative position between the first intersection and the second intersection, the first position of the radiation isocenter with respect to the first intersection, and the second position of the treatment isocenter with respect to the second intersection.

For illustration purposes, the following descriptions are described with reference to the determination of the vertical offset $O_2$ along the Z-axis direction (i.e., a vertical distance between the radiation isocenter and the treatment isocenter at the set-up position), and not intended to limit the scope of the present disclosure. For example, the processing device 140 may determine that the first intersection has a Z coordinate (e.g., the average value of the Z-coordinates of the first intersection points is equal to Z); the second intersection has a Z' coordinate (e.g., the average value of the Z-coordinates of the second intersection point is equal to Z'); the difference between the Z-coordinate of the radiation isocenter and the first intersection is $\Delta Z$; and the difference between the Z-coordinate of the second intersection and the treatment isocenter is $\Delta Z'$. In such cases, the processing device 140 may determine that a vertical offset from the radiation isocenter to the treatment isocenter is equal to $(Z-Z'+\Delta Z+\Delta Z')$. A negative vertical offset from the radiation isocenter to the treatment isocenter may indicate that the radiation isocenter is located below the treatment isocenter, while a positive vertical offset from the radiation isocenter to the treatment isocenter may indicate that the radiation isocenter is located above the treatment isocenter. The offset $O_1$ along the Z-axis direction may then be determined based on the vertical offset from the radiation isocenter to the treatment isocenter. In some embodiments, the offset $O_1$ between the treatment position and the set-up position may be represented by a couch encoder offset from an encoder position of the couch at the set-up position to a target encoder position of the couch at the treatment position.

In 804, the processing device 140 (e.g., the determination module 503) may determine the treatment position based on the offset $O_1$ and the set-up position.

The treatment position may be determined so that the offset $O_1$ may be compensated for to align treatment isocenter with the radiation isocenter and/or align the second intersection of the positioning line with the X-Z plane. Optionally, the treatment position may be represented by the target encoder position of the couch. The processing device 140 may cause the couch to move to the target encoder position so that the subject may be moved to the treatment position.

In some embodiments, operations 803 and/or 804 may be performed by the processing device 140 according to data analysis when the subject is still located at the imaging position. For example, the processing device 140 may determine the horizontal distance between the radiation isocenter and the treatment isocenter at the imaging position, and designate the determined distance as the horizontal offset $O_2$ along the X-axis direction. Similarly, the vertical distance between the radiation isocenter and the treatment isocenter at the imaging position may be determined as the vertical offset $O_2$ along the Z-axis direction. As another example, the longitudinal distance between the radiation isocenter and the treatment isocenter at the imaging position may be equal to the longitudinal distance (denoted as D) between the first intersection of the positioning line is at the set-up position and the second intersection of the positioning line is at the imaging position. The processing device 140 may determine the distance D, and determine the longitudinal offset $O_2$ along the Y-axis direction by subtracting the longitudinal distance between the set-up position and the imaging position from the distance D. After the offset $O_2$ and the treatment position are determined, the processing device 140 may cause the couch to move the subject from the imagining position to the treatment position.

In some embodiments, in 801, the first position of the radiation isocenter with respect to the positioning line when the subject is at the setup position may be represented by the first intersection (e.g., the plane 705 as shown in FIG. 7) of the N-shape positioning line, a horizontal distance of the radiation isocenter with respect to a first intersection point at an edge of the N-shape positioning line (e.g., the point A or C as shown in FIG. 7), and a vertical distance of the radiation isocenter with respect to the first intersection point. In 802, the second position of the treatment isocenter with respect to the positioning line when the subject is at the imaging position may be represented by the second intersection of the N-shape positioning line, a horizontal distance of the treatment isocenter with respect to a second intersection point at an edge of the N-shape positioning line, a vertical distance of the treatment isocenter with respect to the second intersection point. So when the subject is brought back to the setup position, the position of the radiation isocenter may be known. Due to N-shape, a longitudinal offset along the Y-axis direction between the radiation isocenter and the treatment isocenter may be determined by determining a longitudinal distance between the first intersection and the second intersection. A horizontal offset along the X-axis direction between the radiation isocenter and the treatment isocenter may be determined based on the horizontal distance of the radiation isocenter with respect to the first intersection point and the horizontal distance of the treatment isocenter with respect to the second intersection point. A vertical offset along the Z-axis direction between the radiation isocenter and the treatment isocenter may be determined based on the vertical distance of the radiation isocenter with respect to the first intersection point and the vertical distance of the treatment isocenter with respect to the second intersection point. An offset vector from the treatment isocenter to the radiation isocenter may be determined. After the couch is brought back to the setup position, it may be moved further by the offset vector, so that the treatment isocenter may align with the radiation isocenter.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure.

However, those variations and modifications do not depart from the scope of the present disclosure. In some embodiments, the process 800 may be accomplished with one or more additional operations not described and/or without one or more of the operations discussed above. In some embodiments, two or more operations may be combined into a single operation. For example, operations 803 and 804 may be combined into a single operation.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially."For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for treatment positioning, comprising:
    a treatment component for treating a target of a subject, the treatment component including a radiation source that has a radiation isocenter;
    an imaging component;
    a couch being movable between the treatment component and the imaging component along a reference axis, the couch including a positioning line that has a positioning feature, the positioning feature having a plurality of feature values, each feature value corresponding to a unique cross section of the couch, the unique cross section being at an oblique angle with the reference axis;
    at least one storage device storing a set of instructions; and
    at least one processor configured to communicate with the at least one storage device, wherein when executing the set of instructions, the at least one processor is configured to direct the system to perform operations including:
        acquiring, using the radiation source of the treatment component, at least one first image relating to the subject and the positioning line, the subject being located at a set-up position with respect to the treatment component during the acquisition of the at least one first image;
        acquiring, using the imaging component, at least one second image relating to the subject and the positioning line, the subject being located at an imaging position with respect to the imaging component during the acquisition of the at least one second image;
        determining, based on the at least one second image, a treatment isocenter of the target; and
        determining, based on the at least one first image, the at least one second image, and the positioning line, a treatment position of the subject at which a treatment session is delivered by the treatment component to the target of the subject, wherein the treatment isocenter of the target aligns with the radiation isocenter when the subject is located at the treatment position.

2. The system of claim 1, wherein to determine a treatment position of the subject, the at least one processor is further configured to direct the system to perform the operations including:
    determining, based on the at least one first image, a first position of the radiation isocenter with respect to the positioning line during the acquisition of the at least one first image;
    determining, based on the at least one second image, a second position of the treatment isocenter with respect to the positioning line during the acquisition of the at least one second image; and
    determining, based on the first position, the second position, and the positioning line, the treatment position of the subject.

3. The system of claim 2, wherein to determine the treatment position of the subject based on the first position, the second position, and the positioning line, the at least one processor is further configured to direct the system to perform the operations including:
    determining, based on the first position, the second position, and the positioning line, an offset between the set-up position and the treatment position; and
    determining, based on the offset and the set-up position, the treatment position.

4. The system of claim 2, wherein the at least one first image includes a plurality of two-dimensional (2D) images relating to a first intersection between the positioning line and an isocentric plane of the treatment source when the subject is located at the set-up position, the isocentric plane passing through the radiation isocenter and being perpendicular to the reference axis, and
    to determine a first position of the radiation isocenter with respect to the positioning line during the acquisition of the at least one first image, the at least one processor is further configured to direct the system to perform the operations including at least one of:
        determining, based on the plurality of 2D images, a position of the radiation isocenter with respect to the first intersection; or
        determining, based on at least one of the plurality of 2D images, an angular orientation of the positioning line with respect to the reference axis.

5. The system of claim 2, wherein the at least one second image includes a three-dimensional (3D) image of the subject, and
    to determine a second position of the treatment isocenter with respect to the positioning line during the acquisition of the at least one second image, the at least one processor is further configured to direct the system to perform the operations including:
        identifying, from the 3D image of the subject, an image plane that passes through the treatment isocenter and is perpendicular to the reference axis;
        determining a second intersection between the image plane and the positioning line when the subject is located at the imaging position; and
        determining a position of the treatment isocenter with respect to the second intersection.

6. The system of claim 1, wherein the at least one processor is further configured to direct the system to perform the operations including:
    placing the subject at the set-up position before the acquisition of the at least one first image; and causing the couch to move the subject from the set-up position to the imaging position after the acquisition of the at least one first image and before the acquisition of the at least one second image.

7. The system of claim 1, wherein:
the treatment component includes a megavoltage (MV) treatment source as the radiation source, or
the treatment component includes an MV treatment source and a kilovoltage (KV) radiation source, and the radiation source is the KV radiation source.

8. The system of claim 1, wherein the imaging component is a fan-beam computed tomography (FBCT) device.

9. The system of claim 1, wherein the positioning line has one of an N-shape, an S-shape, a V-shape, a W-shape, a triangle, a trapezoid, a polygon, or an irregular shape.

10. A method for treatment positioning implemented on a system, the system comprising:
a treatment component for treating a target of a subject, the treatment component including a radiation source that has a radiation isocenter;
an imaging component; and
a couch being movable between the treatment component and the imaging component along a reference axis, the couch including a positioning line that has a positioning feature, the positioning feature having a plurality of feature values, each feature value corresponding to a unique cross section of the couch, the unique cross section being at an oblique angle with the reference axis, the method comprising:
acquiring, using the radiation source of the treatment component, at least one first image relating to the subject and the positioning line, the subject being located at a set-up position with respect to the treatment component during the acquisition of the at least one first image;
acquiring, using the imaging component, at least one second image relating to the subject and the positioning line, the subject being located at an imaging position with respect to the imaging component during the acquisition of the at least one second image;
determining, based on the at least one second image, a treatment isocenter of the target; and
determining, based on the at least one first image, the at least one second image, and the positioning line, a treatment position of the subject at which a treatment session is delivered by the treatment component to the target of the subject, wherein the treatment isocenter of the target aligns with the radiation isocenter when the subject is located at the treatment position.

11. The method of claim 10, wherein the determining a treatment position of the subject further comprises:
determining, based on the at least one first image, a first position of the radiation isocenter with respect to the positioning line during the acquisition of the at least one first image;
determining, based on the at least one second image, a second position of the treatment isocenter with respect to the positioning line during the acquisition of the at least one second image; and
determining, based on the first position, the second position, and the positioning line, the treatment position of the subject.

12. The method of claim 11, wherein the determining the treatment position of the subject based on the first position, the second position, and the positioning line further comprises:

determining, based on the first position, the second position, and the positioning line, an offset between the set-up position and the treatment position; and
determining, based on the offset and the set-up position, the treatment position.

13. The method of claim 11, wherein the at least one first image includes a plurality of two-dimensional (2D) images relating to a first intersection between the positioning line and an isocentric plane of the radiation source when the subject is located at the set-up position, the isocentric plane passing through the radiation isocenter and being perpendicular to the reference axis, and
the determining a first position of the radiation isocenter with respect to the positioning line during the acquisition of the at least one first image further comprises:
determining, based on the plurality of 2D images, a position of the radiation isocenter with respect to the first intersection; or
determining, based on at least one of the plurality of 2D images, an angular orientation of the positioning line with respect to the reference axis.

14. The method of claim 11, wherein the at least one second image includes a three-dimensional (3D) image of the subject, and
the determining a second position of the treatment isocenter with respect to the positioning line during the acquisition of the at least one second image further comprises:
identifying, from the 3D image of the subject, an image plane that passes through the treatment isocenter and is perpendicular to the reference axis;
determining a second intersection between the image plane and the positioning line when the subject is located at the imaging position; and
determining a position of the treatment isocenter with respect to the second intersection.

15. The method of claim 10, further comprising:
placing the subject at the set-up position before the acquisition of the at least one first image; and
causing the couch to move the subject from the set-up position to the imaging position after the acquisition of the at least one first image and before the acquisition of the at least one second image.

16. The method of claim 10, wherein:
the treatment component includes a megavoltage (MV) treatment source as the radiation source, or
the treatment component includes an MV treatment source and a kilovoltage (KV) radiation source, and the radiation source is the KV radiation source.

17. The method of claim 10, wherein the imaging component is a fan-beam computed tomography (FBCT) device.

18. The method of claim 10, wherein the positioning line has one of an N-shape, an S-shape, a V-shape, a W-shape, a triangle, a trapezoid, a polygon, or an irregular shape.

19. A non-transitory computer readable medium, comprising at least one set of instructions for treatment positioning in a system, the system comprising a treatment component for treating a target of a subject, the treatment component including a radiation source that has a radiation isocenter; an imaging component; and a couch being movable between the treatment component and the imaging component along a reference axis, the couch including a positioning line that has a positioning feature, the positioning feature having a plurality of feature values, each feature value corresponding to a unique cross section of the couch, the unique cross section being at an oblique angle with the reference axis, wherein when executed by one or more processors of the system, the at least one set of instructions causes the system to perform a method comprising:

acquiring, using the radiation source of the treatment component, at least one first image relating to the subject and the positioning line, the subject being located at a set-up position with respect to the treatment component during the acquisition of the at least one first image;

acquiring, using the imaging component, at least one second image relating to the subject and the positioning line, the subject being located at an imaging position with respect to the imaging component during the acquisition of the at least one second image;

determining, based on the at least one second image, a treatment isocenter of the target; and determining, based on the at least one first image, the at least one second image, and the positioning line, a treatment position of the subject at which a treatment session is delivered by the treatment component to the target of the subject, wherein the treatment isocenter of the target aligns with the radiation isocenter when the subject is located at the treatment position.

20. The non-transitory computer readable medium of claim 19, wherein the determining a treatment position of the subject further comprises:

determining, based on the at least one first image, a first position of the radiation isocenter with respect to the positioning line during the acquisition of the at least one first image;

determining, based on the at least one second image, a second position of the treatment isocenter with respect to the positioning line during the acquisition of the at least one second image; and determining, based on the first position, the second position, and the positioning line, the treatment position of the subject.

* * * * *